(12) United States Patent
Tefiku et al.

(10) Patent No.: US 11,950,914 B2
(45) Date of Patent: *Apr. 9, 2024

(54) INTEGRATED ECG ELECTRODE AND ANTENNA RADIATOR

(71) Applicant: Fitbit, Inc., San Francisco, CA (US)

(72) Inventors: Faton Tefiku, San Diego, CA (US); Yonghua Wei, San Diego, CA (US); Kevin Li, San Diego, CA (US); Man-Chi Liu, San Francisco, CA (US); Lindsey Michelle Sunden, San Francisco, CA (US); Peter W. Richards, San Francisco, CA (US); Dennis Jacob McCray, San Diego, CA (US); Christos Kinezos Ioannou, San Diego, CA (US); Kyung Nim Noh, San Francisco, CA (US)

(73) Assignee: Fitbit, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/991,458

(22) Filed: Nov. 21, 2022

(65) Prior Publication Data
US 2023/0157610 A1    May 25, 2023

Related U.S. Application Data

(63) Continuation of application No. 17/072,561, filed on Oct. 16, 2020, now Pat. No. 11,504,043, which is a
(Continued)

(51) Int. Cl.
*A61B 5/304*    (2021.01)
*A61B 5/00*     (2006.01)
(Continued)

(52) U.S. Cl.
CPC ............ *A61B 5/304* (2021.01); *A61B 5/0006* (2013.01); *A61B 5/25* (2021.01); *A61B 5/681* (2013.01); *H01Q 1/50* (2013.01); *H03H 7/38* (2013.01)

(58) Field of Classification Search
CPC ......... A61B 5/304; A61B 5/0006; A61B 5/25; A61B 5/681; A61B 5/00; A61B 5/305; A61B 5/308; H01Q 1/50; H03H 7/38
See application file for complete search history.

(56) References Cited

U.S. PATENT DOCUMENTS 6,647,286 B1    11/2003  Kato et al.
8,301,232 B2    10/2012  Albert et al.
(Continued)

FOREIGN PATENT DOCUMENTS

JP    2002/125943 A    5/2002

OTHER PUBLICATIONS

International Search Report and Written Opinion for PCT/US2019/039975, dated Oct. 25, 2019.
(Continued)

*Primary Examiner* — Paula J Stice
(74) *Attorney, Agent, or Firm* — Dority & Manning, P.A.

(57) ABSTRACT

Multiple circuits in a computing device can share one or more conductive elements. The use of the conductive element can vary by circuit, such as an antenna radiator for a radio frequency (RF) circuit or an electrode for an electrocardiography (ECG) circuit. The circuitry sharing a conductive element can utilize signals obtained over different frequency ranges. Those ranges can be used to select decoupling circuitry, or elements, that can enable the respective circuits to obtain signals over a respective frequency range, excluding signals over one or more other frequency ranges corresponding to other circuitry sharing the circuit. Such an
(Continued)

approach allows for concurrent independent operation of the circuitry sharing a conductive element.

14 Claims, 7 Drawing Sheets

Related U.S. Application Data continuation of application No. 16/457,337, filed on Jun. 28, 2019, now Pat. No. 10,806,362.

(60) Provisional application No. 62/697,844, filed on Jul. 13, 2018.

(51) Int. Cl.
*A61B 5/25* (2021.01)
*H01Q 1/50* (2006.01)
*H03H 7/38* (2006.01)

(56) References Cited

U.S. PATENT DOCUMENTS

| | | |
|---|---|---|
| 8,509,882 B2 | 8/2013 | Albert et al. |
| 2005/0027204 A1 | 2/2005 | Kligfield et al. |
| 2015/0091764 A1 | 4/2015 | Hsieh et al. |
| 2016/0013817 A1 | 1/2016 | Park et al. |
| 2016/0062417 A1 | 3/2016 | Chu et al. |
| 2018/0056080 A1 | 3/2018 | Reinke et al. |
| 2018/0228370 A1 | 8/2018 | Wang et al. |
| 2021/0075089 A1* | 3/2021 | Chang .................. H01Q 21/28 |

OTHER PUBLICATIONS

Webb, "Thermal Transport Characteristics of Human Skin Measured in Vivo Using Ultrathin Conformal Arrays of Thermal Sensors and Actuators", PLoS ONE, Feb. 6, 2015, vol. 10, No. 2, 17 pages.
Kardia.com, https://www.alivecor.com/kardiamobile, retrieved Jul. 10, 2023, 10 pages.

* cited by examiner

INTEGRATED ECG ELECTRODE AND ANTENNA RADIATOR

CROSS-REFERENCE TO RELATED APPLICATION

This application claims priority to Non-Provisional patent application Ser. No. 17/072,561 filed Oct. 16, 2020, now U.S. Pat. No. 11,504,043, and entitled "INTEGRATED ECG ELECTRODE AND ANTENNA RADIATOR, which said application claims priority to Non-Provisional patent application Ser. No. 16/457,337 filed Jun. 28, 2019, now U.S. Pat. No. 10,806,362, and entitled "INTEGRATED ECG ELECTRODE AND ANTENNA RADIATOR" which said application claims priority to and the benefit of U.S. Provisional Patent Application No. 62/697,844, filed Jul. 13, 2018, which are all hereby incorporated by reference herein in their entirety.

BACKGROUND

Recent advances in technology, including those available through consumer devices, have provided for corresponding advances in health detection and monitoring. For example, devices such as fitness bands and smart watches are able to determine information relating to the health of a person wearing the device. It is desirable to be able to provide as much functionality as possible, but the limited form factor of these devices makes it challenging to include the necessary components.

BRIEF DESCRIPTION OF THE DRAWINGS

Various embodiments in accordance with the present disclosure will be described with reference to the drawings, in which.

DETAILED DESCRIPTION

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described. Incorporated by reference, in its entirety, is "METHODS AND SYSTEMS FOR COMBINATION ELECTRODES FOR WEARABLE DEVICES," filed Jun. 28, 2019.

Approaches in accordance with various embodiments provide for the concurrent and independent operation of circuits of a computing device that share at least one conductive element. These can include circuits for communication, such as antenna circuits, as well as circuits for making biometric or physiological measurements for a user. The use of the conductive element can vary by circuit, such as an antenna radiator for a radio frequency (RF) circuit or a dry electrode for an electrocardiography (ECG) circuit. The circuitry sharing a conductive element can utilize signals obtained over different frequency ranges. Those ranges can be used to select decoupling circuitry (or elements) that can enable the respective circuits to obtain signals over a respective frequency range and exclude signals over one or more other frequency ranges corresponding to other circuitry sharing the circuit. Such an approach allows for concurrent independent operation of the various circuits sharing a conductive element.

Various other functions can be implemented within the various embodiments as well as discussed and suggested elsewhere herein.

Figure 1:
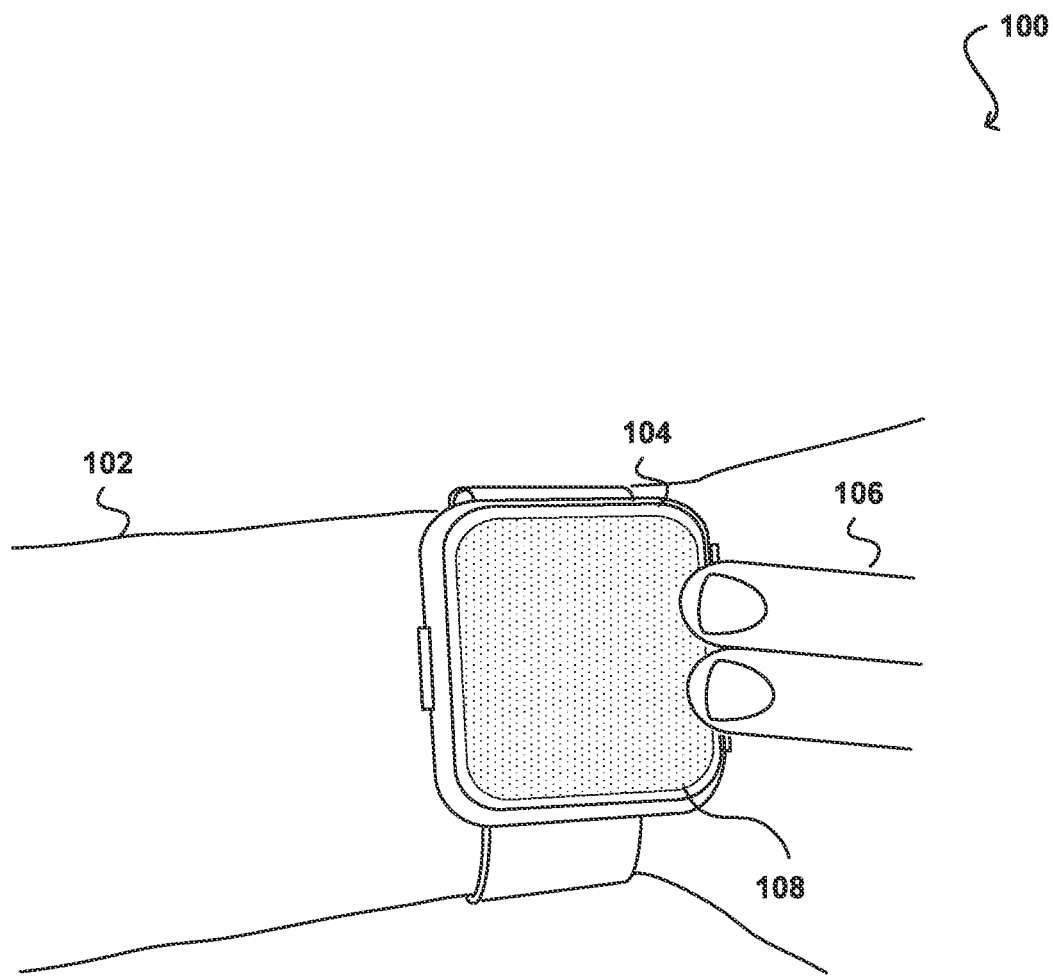
FIG. 1 illustrates an example device that can be utilized in accordance with various embodiments.

FIG. 1 illustrates an example wearable device 100 that can be utilized in accordance with various embodiments. In this example the device is a smart watch, although fitness trackers and other types of devices can be utilized as well. Further, although this device is shown to be worn on a user's wrist there can be other types of devices worn on, or proximate to, other portions of a user's body as well, such as on a finger, in an ear, around a chest, etc. For many of these devices there will be at least some amount of wireless connectivity, enabling data transfer between a networked device or computing device and the wearable device. This might take the form of a Bluetooth connection enabling specified data to be synchronized between a user computing device and the wearable device. A cellular or Wi-Fi connection can be used to transmit data across at least one network such as the Internet or a cellular network, among other such options.

As mentioned, there can be various other types of functionality offered by such a wearable device, as may relate to the health of a person wearing the device. One such type of functionality relates to electrocardiography (ECG). ECG is a process that can be used to determine and/or track the activity of the heart of a person over a period of time. In order to obtain ECG data, a conductive electrode is often brought into contact with the skin of the person to be monitored. In the example situation of FIG. 1, a person is wearing a wearable device 100 on his or her arm 102, and can bring one or more fingers 106 (or palm, etc.) into contact with an exposed electrode of the device. In this example, the electrode is at least a portion of a metallic ring 104 that is part of the housing around a display screen 108 of the wearable device, although other types and forms of electrodes can be used as well within the scope of the various embodiments. The electrode can be connected to an ECG circuit that can detect small changes in electrical charge on the skin that vary with the user's heartbeat. ECG data can be monitored over time to attempt to determine irregularities in heartbeat that might indicate serious cardiac issues. Conventional ECG measurements are obtained by measuring the electrical potential of the heart over a period of time, typically corresponding to multiple cardiac cycles. By a user placing his or her fingers on the exposed electrode for a minimum period of time, during which ECG measurements are taken, an application executing on the wearable device can collect and analyze the ECG data and provide feedback to the user.

As mentioned, however, space for additional elements in such a device can be limited. There may be other relevant considerations as well, as may relate to weight, resource costs, manufacturing capabilities, or appearance. These limits must be balanced with the needs or desires to support multiple communications protocols, as may include Bluetooth, Wi-Fi, GNSS, and LTE Cat-M1, among others. The ability to concurrently support multiple communications protocols in some embodiments can benefit from the use of multiple antennas. Each additional antenna, however, requires space on, or in, the device. It therefore can be desirable to attempt to reduce or minimize the number of elements required. When measuring ECG as discussed above, an electrode can be used that can take the form of a large metal element, or other element of a sufficiently conductive material. Since the ECG frequencies are sufficiently different than the frequencies for the various communications protocols, approaches discussed herein can utilize one or more ECG electrodes as communications antenna elements. Such an approach can reduce the number of elements (including separate antenna(s) and electrode(s)) needed to support the same functionality on a specific device.

Figure 2A:
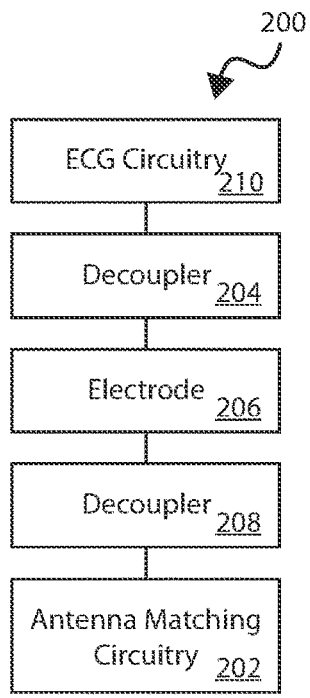
FIGS. 2A and 2B illustrate general components of a shared ECG circuitry and electrode system that can be utilized in accordance with various embodiments.

FIG. 2A illustrates a simplified block diagram 200 of one such implementation that can be utilized in accordance with various embodiments. This diagram illustrates antenna matching circuitry 202 and ECG circuitry 210, which each can include any appropriate circuitry known, used, or appropriate for such functionality, including but not limited to those discussed herein. The antenna matching circuitry 202 and ECG circuitry 210 can share a single electrode 206 in this example, although other combinations or approaches can be used as well within the scope of the various embodiments. For many ECG implementations, at least one electrode 206 must be isolated from extended contact with the skin of the user, such as from the wrist upon which a smart watch or fitness tracking device might be worn. An example electrode is metallic and of a sufficiently large size, at least relative to the size of the device, in order to allow for good contact with the skin of the user. In one example embodiment, an electrode has a size on the order of at least 150 $mm^2$. Such electrode can be made of stainless steel, although any conductive metal material or metal alloy may be considered as long as the contact surface is not subject to oxidation during exposure to air or moisture. Where multiple communication protocols or standards are utilized, the antenna radiators may need to occupy a large portion of the volume within or on the device. The antenna circuitry is typically placed relatively close to the antenna radiator or electrode, while there may be no restriction or advantage to placing ECG circuitry relatively close to the antenna circuitry. The ECG circuitry can be placed at an optimal location for the particular device design. An approach such as that illustrated in FIG. 2A enables at least one metallic piece, or other conductive element, to be utilized concurrently as an ECG electrode and an antenna radiator. As discussed elsewhere herein, additional circuits that utilize similar conductive elements might share such an element as well, such as where the frequency range to be analyzed for a circuit or application falls sufficiently outside the frequency range of any other circuit or application sharing a particular electrode. There may also be more than two circuits sharing a single conductive element, or set of conductive elements, within the scope of the various embodiments. The sharing of such components can save significant space on, or within, such a device where separate elements of this size might otherwise be required.

In the example system of FIG. 2A, the ECG circuitry 210 is connected to the shared electrode 206 (also functioning as an antenna radiator) via a decoupling circuit or element 208 that isolates the ECG circuitry 210 over a range of radio frequency (RF) frequencies (around 700 MHz to around 3 GHz, or above 600 MHZ for at least some embodiments utilizing LTE Cat M1, GNSS, Bluetooth, and Wi-Fi protocols, or up to about 6 GHz in other embodiments) from the antenna matching circuitry 202, which can be connected to one or more RF systems. The antenna matching circuitry 202 can be connected to the shared electrode/radiator 206 via a second decoupling circuit or element 204 that isolates it at a range of low frequencies (around 0 Hz (DC) to around 150 kHz for some embodiments, although for sufficient isolation a higher cutoff frequency can be utilized) from the ECG circuitry 210. The impact of the ECG circuit on the antenna matching circuit can be reduced by using inductors or ferrite beads that have high impedance at RF frequencies instead of high impedance resistors as discussed elsewhere herein. Since ECG circuitries have high impedance inputs, the relatively lower impedance decoupling component 208 will have a negligible impact on the ECG system in at least some embodiments. Additional isolation can be achieved in some embodiments by using a shunt capacitor to ground after the series resistor/inductor that would present a short circuit to ground at RF frequencies. By achieving good isolation at their respective frequencies of operation between the ECG circuit and antenna matching circuit with the first few components of each circuit, other parts of the ECG circuit can be more easily designed and optimized without affecting the antenna matching circuit, and vice versa. Decoupling the circuits also enables them to function independently in at least some embodiments, although in other embodiments the conductive elements might be shared but only operated one at a time for a specific circuit, such as where a specific communication protocol utilizes a frequency range that is relatively close to that of the ECG circuit or other circuit sharing the conductive element. If there are more than two circuits sharing such an element, then any subset of the circuits that are decoupled can concurrently utilize the element at a specific time.

Decoupling elements can be used to filter or otherwise attenuate signals from one circuitry element to another. For example, one decoupling element can cause the ECG signal to not significantly load the communications circuitry (and/or vice versa), providing a few tenths of a decibel of load (e.g., 0.1 dB, 0.2 dB, 0.3 dB, 0.4 dB, or 0.5).

Figure 2B:
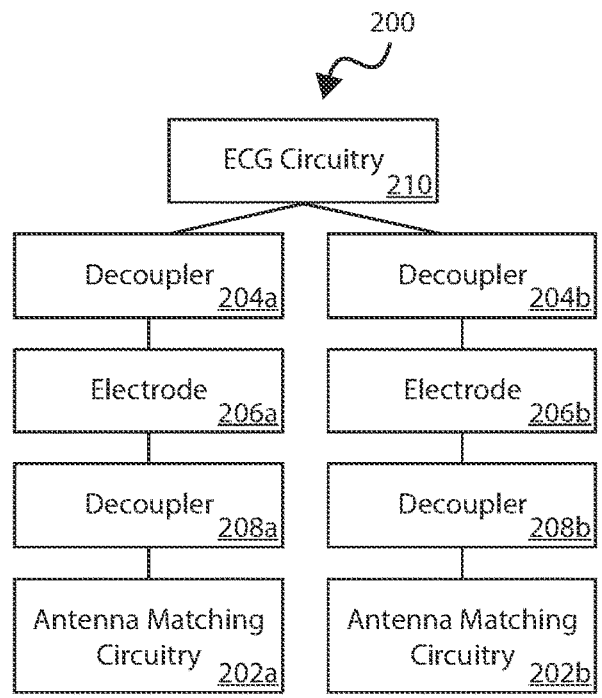

FIG. 2B illustrates an example alternative to FIG. 2A whereby there are two electrodes 206a and 206b each connected to respective antenna matching circuitry 202a and 202b using respective decouplers 204a, 204b, 208a, and 208b. The two electrodes can then be connected to a single ECG circuitry element 210.

Figure 3:
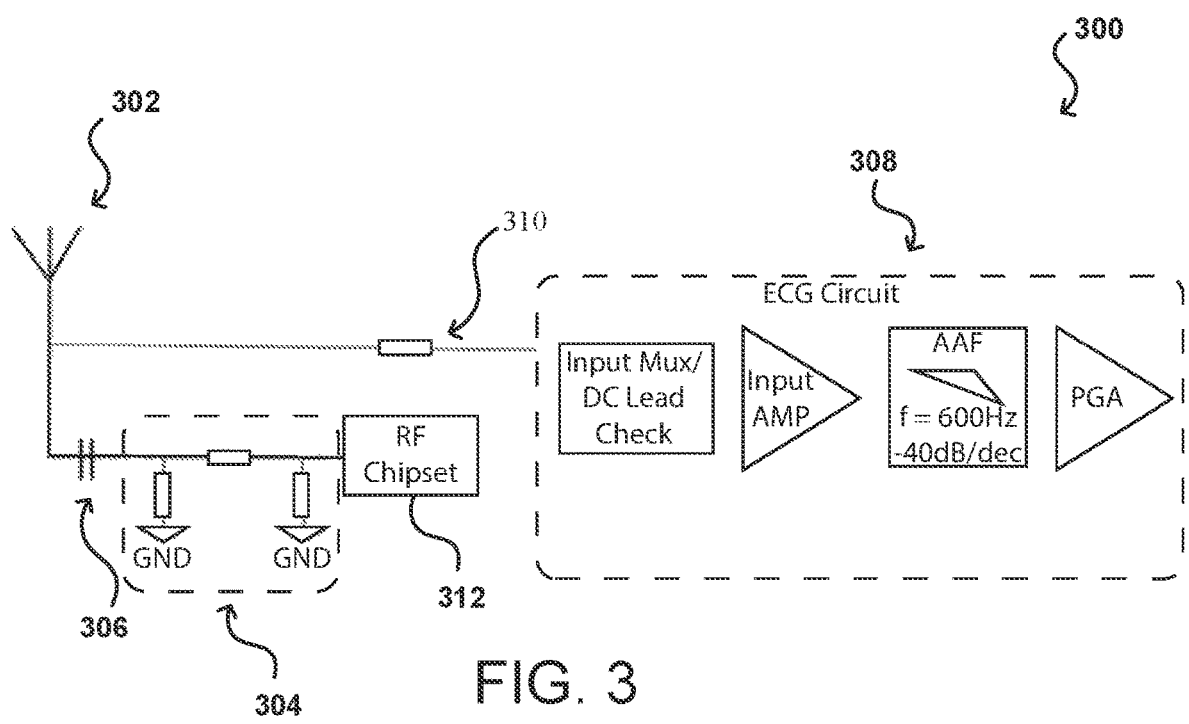
FIG. 3 illustrates a first example implementation that can be utilized in accordance with various embodiments.

FIG. 3 illustrates a first example subsystem 300 that can be utilized in accordance with various embodiments. In this example a conductive element 302 is shared as an electrode for an ECG circuit 308 and a radiator for an antenna matching circuit 304. The ECG circuit and antenna matching circuit can be on the same or different printed circuit boards (PCB), chips, etc., in various embodiments. This example represents a monopole antenna concept wherein there is no ground path from the antenna radiator to system PCB ground. In this example, a first decoupling element 306 is positioned between the shared conductive element 302 and the antenna matching circuit 304, which in turn feeds into an RF chipset 312. The first decoupling element 306 is selected based at least in part upon the relative operating frequencies of the ECG circuit and the antenna matching circuit, such that only frequencies within the range for the antenna matching circuit are passed along to the antenna matching circuit 304, or at least that frequencies in the range for the ECG circuit are not significantly passed along to the antenna matching circuit 304. There may be some amount of cross-talk between the signals of the two frequency ranges, but such cross-talk is negligible in some embodiments, or can be accounted for in others. Such cross-talk can be digitally attenuated as part of a signal analysis procedure. A second decoupling element 310 can be selected based at least in part upon the relative operating frequencies of the ECG circuit and the antenna matching circuit, such that only frequencies within the range for the ECG are passed along to the ECG circuit 308, or at least that frequencies in the range for the antenna matching circuit are not significantly passed along to the ECG circuit 308. Although specific components are illustrated for the ECG and antenna matching circuits, as mentioned elsewhere herein any appropriate circuitry known, used, or developed for such purposes can be utilized as well within the scope of the various embodiments. As at least some circuits of these types are well known in the art, they will not be discussed in detail herein. In one embodiment, the first decoupling element 306 (or circuit) is a 33 pF capacitor aligned in series for decoupling of the ECG signal, although other capacitors can be used as well in various embodiments, such as capacitors with values between about 20 pF and about 100 pF, or even values up to 100 nF. The second decoupling element 310 (or circuit) in this example is a 22 k resistor used for RF antenna decoupling, which in various embodiments is preferred to be placed closer to the conductive element 302 in this embodiment. This decoupling element can alternatively be a resistor having a value between 5K ohms and 100K ohms, or an inductor with a value between about 30 nH to about 1 uH in some embodiments, or a ferrite bead which provides 1000 ohms or high impedance at the operating frequencies of the antenna matching circuit. A second contact point for the ECG circuit 308 as illustrated can be connected to a second electrode that is not shared with the first decoupling element 306. In this example the capacitor of the first decoupling circuit 306 provides an open circuit for the signals at the ECG frequency, and the resistor of the second decoupling element 310 will only allow signals at the antenna frequency to pass to the antenna matching circuit.

As discussed herein, the first and second decoupling elements (or circuits) can be any appropriate decoupling elements capable of filtering out specific frequencies, or allowing only specific frequencies, to be propagated from a shared conductive element. The decoupling elements (or circuits) can include elements such as resistors, inductors, capacitors, and ferrite beads, which can have values or ranges as specified herein. As mentioned, the values can be determined based at least in part upon the respective circuit to which a range of frequencies are to pass, and other circuits sharing the conductive element whose frequencies are not to pass via the decoupling element (or circuit).

Figure 4:
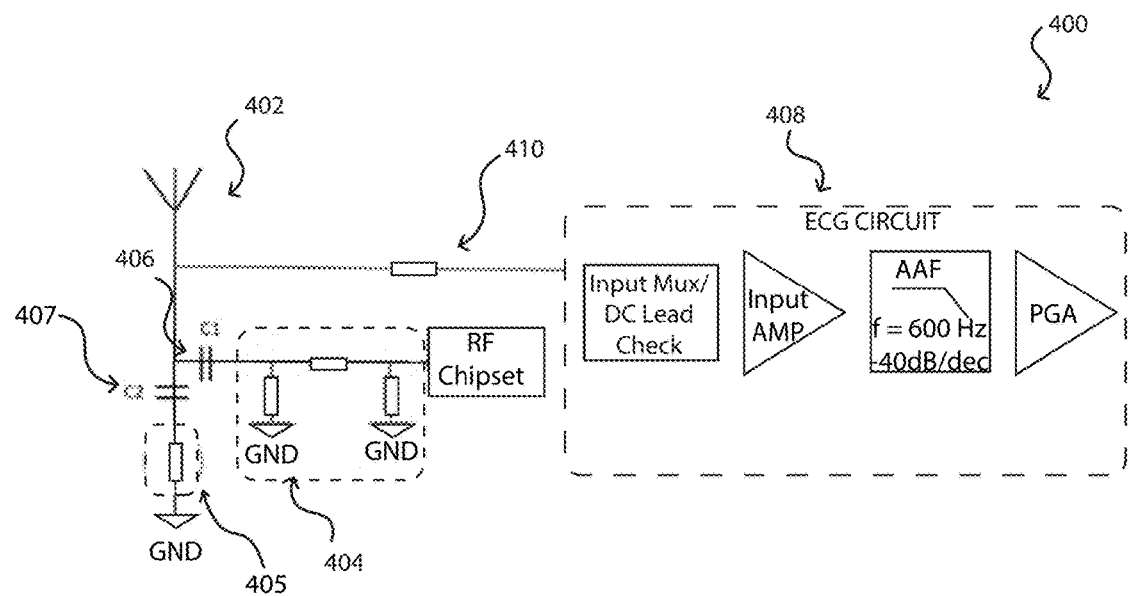
FIG. 4 illustrates a second example implementation that can be utilized in accordance with various embodiments.

FIG. 4 illustrates another example subsystem 400 that can be utilized in accordance with various embodiments. In this example a conductive element 402 is shared as an electrode for an ECG circuit 408, via a respective decoupling element 410 (or circuit), and a radiator for with antenna matching circuits 404 and 405, via a pair of decoupling elements 406 and 407. In this example, the antenna is of a different type that that of FIG. 3, being a loop antenna, slot antenna, or inverted-F antenna (IFA), among other such options. For this type of antenna one or more ground paths are needed from the antenna radiator to the system PCB ground. The two decoupling elements 406 and 407 for the antenna matching circuits 404 and 405 can be of the same type or different types. The two decoupling elements 406 and 407 can have the same value or different values, such as two 33 pF capacitors for decoupling to the ECG signal. The capacitor range can also be the same as is discussed with respect to the corresponding capacitors of FIG. 3. The ECG circuit in this example cannot be DC grounded, which necessitates the capacitive element in each ground path.

Figure 5:
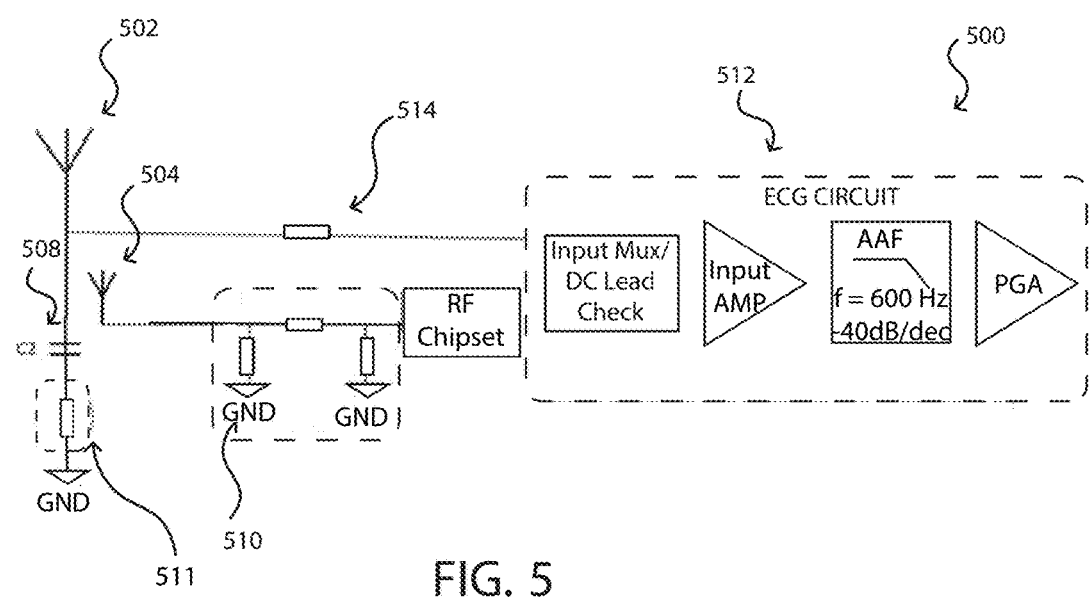
FIG. 5 illustrates a third example implementation that can be utilized in accordance with various embodiments.

FIG. 5 illustrates another example subsystem 500 that can be utilized in accordance with various embodiments. In this example, a conductive element 502 of a pair of conductive elements 502, 504 is shared as an electrode for an ECG circuit 512, via a respective first decoupling element 514. In this example, an electrode 504 can then function as an antenna radiator which is capacitively coupled through a feeding element connected to a first antenna matching circuit 510. The electrode 502 has one or more ground paths to the system PCB ground each via a second decoupling element 508 and a second antenna matching circuit 511. In this example the antenna is of yet a different type, here being a parasitic antenna or capacitive feed antenna that utilizes a ground path to the parasitic radiator or capacitive feed radiator. The capacitive feed antenna can be multiple type of antennas, for example a capacitive feed monopole antenna, a capacitive feed loop antenna, or a capacitive feed slot antenna. A parasitic antenna or a capacitive feed antenna is also referred to as a passive antenna in some situations as it is not electrically connected to any communication circuits on the device. When properly decoupled, the conductive element 502 can function as a passive antenna element. In this example at least a second decoupling element 508 is utilized along each ground path, which can be a capacitor of 33 pF or another such value discussed for such purposes herein.

As mentioned, the electrode or other capacitive element (s) can take many forms on, or in, the device, although for ECG and various other applications at least a portion of the electrode must be exposed or otherwise accessible to the skin of the user. In at least some embodiments, the exposed electrode is utilized with one or more other electrodes that interface with the skin of the wrist or other such location, as may be based upon the type of device or preference of the user. As illustrated in FIG. 1, the electrode can be part of the device housing, or part of a conductive ring around a screen or element of the device. The electrode can also be one or more rods or planar elements positioned at a periphery of the device casing, among other such options. Additionally or alternatively, surface-mounted stainless steel strip can be utilized as an ECG electrode. The electrode strip in one embodiment is adhered to the outside surface of a metal housing but is isolated from the metal housing by one or more layers of adhesive or a non-conductive polybutylene terephthalate (PBT) material manufactured using a process such as nano-molding. As mentioned, for ECG applications this element should not be in contact, or at least extended contact, with the wrist of the user. In some embodiments, nano-molding can be utilized to generate a ring or loop design, where there may be one or more conductive elements, or elements of one or more pieces or regions. In some embodiments there might be multiple splits, such as may correspond to four separate elements, each with a different feed point. Any or all of those elements can be used as electrodes as well, with each capable of being used for at least one different circuit in some embodiments. For example, a top electrode might be used for ECG and Wi-Fi circuitry, while a bottom electrode might be used for LTE communications. There may also be multiple conductive elements utilized for the ECG circuitry, where each element works with a respective antenna circuit, such as for Wi-Fi, 5G, LTE, GNSS, Bluetooth, etc. In some such embodiments, multiple conductive elements utilized for the ECG are utilized by a single antenna circuit and protocol to take advantage of multipathing of signals received/transmitted by the multiple conductive elements (e.g., multi-stream beamforming, spatial multiplexing, and diversity coding as well as other multiple-in and multiple-out (MIMO) or similar techniques). While in many embodiments measurements can be taken concurrently at any time, as discussed in some embodiments where ECG measurements might be taken infrequently, such as only once per day, it might be beneficial to limit communications during that time for a communications circuit utilizing that electrode as an antenna element. For example, the communications circuit can temporarily impose a rate limit or a power limit or otherwise stop communications except for those necessary to maintain the communications link. In some embodiments, certain frequencies or encoding techniques (e.g., quadrature amplitude modulation or orthogonal frequency-division multiplexing) within a communications specification might not be fully filtered by the ECG decoupling element. When ECG measurements are taken, the communications circuitry can minimize use of such frequencies or encoding techniques. For example, a protocol using adaptive frequency-hopping spread spectrum can be programmed to "skip" over frequencies that cause problems for ECG measurement.

Figure 6:
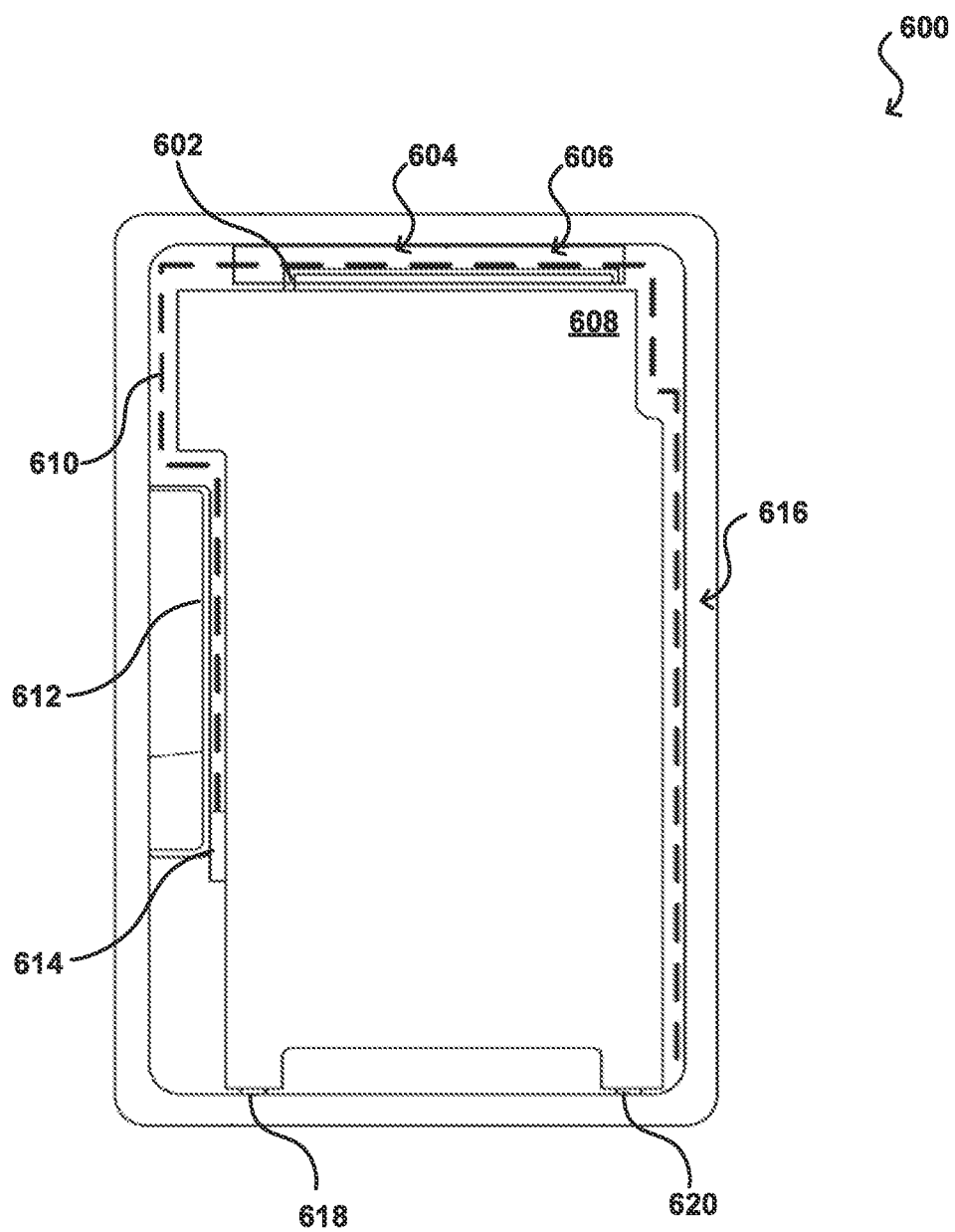
FIG. 6 illustrates components of an example device that can be utilized in accordance with various embodiments.

As mentioned, other designs or types of conductive elements can be used in accordance with various embodiments. For example, FIG. 6 illustrates a top view of an example electronic device 600 having a metal plate 608 within a metal housing 616 forming a slot antenna 610 that is excited by a monopole antenna 606. The housing (such as a metal housing) 616 may be designed to accommodate a display that will be worn on a person's wrist. A wristband (not shown) may be connected to the opposing ends of the metal housing, and the completed unit may be worn on someone's wrist. The metal housing may be designed to conform better to the cross-sectional curvature of a person's forearm and the interior of the metal housing may be occupied by various electrical components, including a PCB or FPCB (Flexible Printed Circuit Board) that includes, for example, various sensors, processors, power management components, etc. The metal housing may include additional features, such as a metal button bracket 612, to support other elements within the metal housing.

The slot antenna 610 is structured as a gap between the metal plate 608 and the metal housing 616 (including the metal button bracket 612) stopped at two ends with grounding contacts 614, 620 between the metal plate and the metal housing. The gap between the metal plate and the metal housing, running between the grounding contacts 614, 620, forms the slot antenna 610 that, when excited by the monopole antenna 606, radiates or receives RF signals. The slot antenna can be configured as a half-wavelength slot antenna (e.g., a length of about 6.25 cm for Bluetooth communication). The slot antenna is not directly driven by any element (e.g., an antenna feed or coaxial cable) coupled to the printed circuit board or other similar component. A third grounding pin 618 can be included to improve performance. The grounding contacts 614, 620 can be used to tune the slot resonance of the slot antenna (e.g., to resonate within the Bluetooth band). The third grounding pin 618 can be used for reducing or preventing unwanted resonances in the remaining gap between the metal housing and the metal plate that may reduce the radiation efficiency of the slot antenna 610. The grounding clips can be configured as a spring contact or other type of electrical connection. The grounding clips can include elements that terminate in a leaf spring that presses against the metal housing or metal button bracket.

The example monopole antenna 606 is designed to excite the slot antenna 610 in a targeted mode. The monopole antenna includes a flex printed circuit board (FPCB) as the monopole radiator 602 on a monopole antenna carrier 604 made of a plastic mechanical component. The FPCB 602 is assembled on the surface of the carrier 604 and the carrier is placed inside the metal housing 616. The carrier can be attached to the metal housing or other component of the device.

Such a device can be used for biometric monitoring in some embodiments, as discussed herein. Biometric monitoring devices, including wrist-worn biometric monitoring devices, can be configured to send and receive biometric and other data to and from one or more separate electronic devices. To wirelessly send and receive data, such monitoring devices require the use of one or more antennas in the device.

An example antenna architecture for wearable electronic devices includes two portions. First, the antenna architectures include a monopole antenna having a monopole radiator on a plastic carrier implemented at a top of a display area within a metal housing of the device. The monopole radiator is connected through an antenna clip on a printed circuit board (PCB) to a radio frequency (RF) engine. The monopole antenna can be implemented as a flex film antenna radiator assembled on, for example, a plastic carrier. The monopole radiator can generate electromagnetic fields to induce the slot antenna to transmit or receive radio frequency signals. The antenna can be designed to be particularly receptive to (or emissive of) radio frequency energy at frequencies within the frequency band(s) for the wireless communications protocol(s) that the antenna is designed to support, and the antenna can also be designed to not be particularly receptive to (or emissive of) radio frequency energy at frequencies outside of the frequency band(s). Antennas may achieve such selectivity by virtue of their physical geometry and the dimensions that define that geometry.

Second, the antenna architectures include a slot antenna formed by a gap between a metal (and/or conductive) plate and the metal housing. The slot antenna radiates RF signals from the slot structure through a display module, a touch module, and a glass window. The monopole radiator and slot antenna are capacitively coupled such that the monopole radiator generates a varying electric field that induces varying electric fields at the slot antenna, resulting in the reception and/or emission of RF signals. This coupling of electric fields between the monopole radiator and the slot antenna allows for RF signals to be transmitted from and received by the device. The monopole radiator is positioned within the slot area to excite the slot antenna through electromagnetic field coupling. The dimensions of the slot antenna and monopole antenna can be tuned to achieve targeted communication frequency bands. Furthermore, the monopole antenna portion can be tuned to have a certain length and a matching circuit on the PCB may be utilized to tune the antenna impedance to achieve targeted performance characteristics. In some embodiments, the metal plate and/or metal housing can be conductive. The metal plate and/or metal housing can include one or more materials that include a conductivity of 1E5 Siemens/m and/or higher.

In some embodiments, the disclosed monopole-excited slot antenna reduces the dead band of the display window or provide a desirably or advantageously small dead band at a top of the display window. The monopole antenna component that excites the slot antenna can provide a targeted excitation for the slot antenna with a reduced distance between a top side of the metal housing and a display module relative to a pure monopole antenna or inverted-F antenna (IFA) architecture with similar antenna performance.

In some embodiments, the disclosed monopole-excited slot antenna accommodates a device architecture having a printed circuit board (PCB) mounted close to the bottom of a metal housing. For tapered metal housings, this allows a relatively large battery to be placed above the PCB and within the metal housing. In contrast, devices with similar tapered metal housings employing other antenna designs may require the PCB to be mounted above the battery to achieve suitable performance, manufacturing costs, and/or mechanical complexity. In such devices, the battery size is reduced relative to devices that incorporate the antenna architectures disclosed herein that allow the battery to be placed above the PCB.

In some embodiments, the disclosed monopole-excited slot antenna design resides entirely within the metal housing. Advantageously, this facilitates manufacturing the device to be water resistant and/or swim proof. Where at least some portion of the antenna is exterior to the metal housing, vias, or holes in the metal housing may be required to send and receive electrical signals to the portion of the antenna outside of the metal housing. These vias or holes may compromise any water-tight capabilities of the device or may undesirably increase the cost of making such a device water resistant and/or swim proof.

In some embodiments, the disclosed monopole-excited slot antenna designs exert no contact pressure force on the glass window. Advantageously, this facilitates manufacturing the device to be water resistant and/or swim proof, creating water-tight seals for junctions between components. Where an antenna exerts an outward force on the display window, for example, the display window may tend to separate from the metal housing, compromising the water-tight seal.

Example monopole-excited slot antenna functions by using a capacitively-coupled monopole antenna radiator to excite an antenna slot. Relative to a device that uses a slot antenna with a direct feed from a PCB to excite the slot antenna, the disclosed antenna design may be advantageous due at least in part to being mechanically simpler (e.g., not requiring the using of a coaxial cable or other transmission line from the PCB to the antenna) resulting in a lower cost and increased ease of manufacture.

Various implementations discussed herein may be used, for example, to provide a monopole-excited slot antenna that provides Bluetooth functionality, including Bluetooth Low Energy (Bluetooth LE or BTLE) functionality. Such a compact and efficient antenna may be of particular use in highly-integrated devices having a small form factor. For example, the disclosed antennas can be used in biometric monitoring devices, e.g., wearable devices that track, report, and communicate various biometric measurements, e.g., distance traveled, steps taken, flights of stairs climbed, etc. Such devices may take the form of a small device that is clipped to a person's clothing or worn on a person's wrist. Such a device may, for example, contain various processors, printed circuit boards, sensors, triaxial accelerometers, triaxial gyroscopes, triaxial magnetometers, an altimeter, a display, a vibramotor, a rechargeable battery, a recharging connector, and an input button all within a metal housing that measures approximately between 1.62" and 2" in length, 0.75" and 0.85" in width, and 0.3" and 0.44" in thickness. A monopole-excited slot antenna may be used in such a device to provide RF communication in a water resistant and/or swim-proof wearable device, to reduce the dead band of a display window, and/or to provide a more cost-efficient and mechanically simple device.

Due to the small size of such devices, monopole-excited slot antennas, such as those disclosed herein, may provide the ability to offer a more compact communications solution than might otherwise be possible, allowing additional volume within the metal housing to be made available for other purposes, such as a larger battery. Such dimensions may prove to be particularly well-suited to RF communications in the Bluetooth wireless protocol bands, e.g., 2402 MHz to 2480 MHz.

Monopole-excited slot antenna antennas that support other wireless communications protocols may also be designed using the principles outlined herein. For example, the disclosed antenna architectures may be configured or dimensioned to be suitable for use with wireless networks and radio technologies, such as wireless wide area network (WWAN) (e.g., cellular) and/or wireless local area network (WLAN) carriers. Examples of such wireless networks and radio technologies include but are not limited to Long Term Evolution (LTE) frequency bands or other cellular communications protocol bands, GPS (Global Positioning System) or GNSS (Global Navigation Satellite System) frequency bands, ANT™, 802.11, and ZigBee™, for example, as well as frequency bands associated with other communications standards. The RF radiator size, gaps between components, and other parameters discussed herein may be adjusted as needed in order to produce a monopole-excited slot antenna, as described herein, that is compatible with such other frequency bands.

In some implementations, embodiments involve antenna configurations for biometric monitoring devices. The term "biometric monitoring device" is used herein according to its broad and ordinary meaning, and may be used in various contexts herein to refer to any type of biometric tracking devices, personal health monitoring devices, portable monitoring devices, portable biometric monitoring devices, or the like. In some embodiments, biometric monitoring devices in accordance with the present disclosure may be wearable devices, such as may be designed to be worn (e.g., continuously) by a person (i.e., "user," "wearer," etc.). When worn, such biometric monitoring devices may be configured to gather data regarding activities performed by the wearer, or regarding the wearer's physiological state. Such data may include data representative of the ambient environment around the wearer or the wearer's interaction with the environment. For example, the data may comprise motion data regarding the wearer's movements, ambient light, ambient noise, air quality, etc., and/or physiological data obtained by measuring various physiological characteristics of the wearer, such as heart rate, perspiration levels, and the like.

In some cases, a biometric monitoring device may leverage other devices external to the biometric monitoring device, such as an external heart rate monitor in the form of an ECG sensor for obtaining cardiovascular information, or a GPS or GNSS receiver in a smartphone may be used to obtain position data, for example. In such cases, the biometric monitoring device may communicate with these external devices using wired or wireless communications connections. The concepts disclosed and discussed herein may be applied to both stand-alone biometric monitoring devices as well as biometric monitoring devices that leverage sensors or functionality provided in external devices, e.g., external sensors, sensors or functionality provided by smartphones, etc.

Below the metal plate is positioned a battery (not shown). The battery can be secured within the metal housing to maintain its relative position within the metal housing. For example, a spacer can be used to maintain a separation between the battery and the metal housing. Below the battery is positioned a component layer on a PCB. The component layer can include microprocessors, RAM (random access memory), ROM (read only memory), ASICs (application specific integrated circuit), FPGAs (field programmable gate array), surface mounted elements, integrated circuits, and the like. The PCB provides electrical components and circuitry that directs and interprets electrical signals for the device. For example, the PCB is electrically coupled to the display and touch modules to interpret touch input and to provide images or information to display. The PCB is coupled to an antenna feed clip that is electrically coupled to the monopole antenna. The PCB can include a ground plane area that forms a ground plane for the monopole antenna. The PCB can include a feed clip area that does not include conductive elements other than where the antenna feed clip is mounted on and electrically coupled to the PCB. For example, the PCB can include a trace that electrically couples the ground plane area to the feed clip area, the feed clip being electrically coupled to the trace in the feed clip area. The ground plane for the monopole antenna may be provided by a large metalized area, conductive traces in a printed circuit board (e.g., the PCB) or flexible printed circuit board, a metal plate and/or surface within the metal housing, etc. The device can also include a vibrating motor to provide haptic feedback or to otherwise mechanically vibrate the device. The PCB can be grounded to the metal housing through one or more grounding screws that electrically couple the PCB to the metal housing. Between the battery and component layer, there is a dielectric gap (e.g. air or plastic or combination of air and plastic) which creates a back cavity for the slot antenna within an enclosed metal housing design. The dielectric gap may vary in height, but must insure isolation between the battery to any component on the component layer.

An alternative configuration includes a slot antenna that is directly fed from the PCB rather than being coupled to a monopole antenna, with the PCB being placed above the battery. In devices with tapered cross-sections, this may undesirably reduce the size of the battery. Another alternative configuration includes a slot antenna that is directly fed from the PCB rather than being coupled to a monopole antenna, with the PCB below the battery. This would require the use of a feed line (e.g., coaxial cable) from the PCB to the metal plate or metal housing near the metal plate to excite the fields between the metal housing and the metal plate. Using a coaxial cable complicates the mechanical implementation and increases the cost of the device. Furthermore, the disclosed antenna architectures can be configured to achieve similar performance characteristics as an elevated feed design using a coaxial cable. Another alternative configuration includes a monopole or IFA antenna outside the metal housing. One drawback of this design is the introduction of additional mechanical complexity and added difficulties in achieving a device that is water resistant and/or swim proof. The antenna feed would typically connect the PCB inside the metal housing to the antenna located outside the metal housing. Accordingly, the disclosed antenna architectures can be housed entirely within the metal housing to facilitate water resistance of the device.

Figure 7:
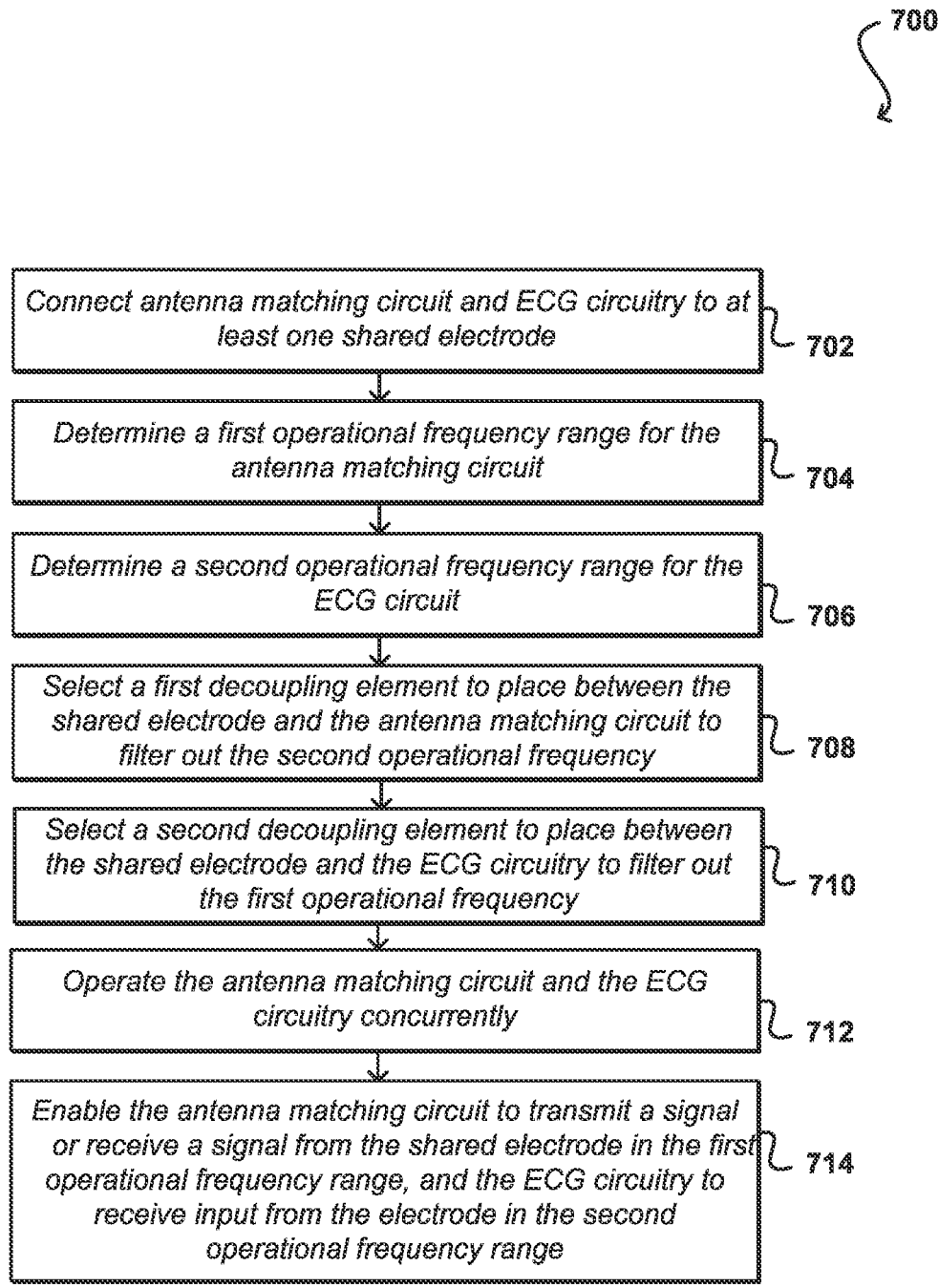
FIG. 7 illustrates an example process for implementing a shared electrode assembly that can be utilized in accordance with various embodiments.

FIG. 7 illustrates an example process 700 for implementing and utilizing a shared conductive element that can be utilized in accordance with one embodiment. It should be understood for this and other processes discussed herein that there can be additional, alternative, or fewer steps performed in similar or alternative orders, or in parallel, within the scope of the various embodiments unless otherwise stated. In this example, an antenna matching circuit and ECG circuitry are connected 702 to at least one shared electrode, antenna radiator, or other such conductive element. A first operational frequency range is determined 704 for the antenna matching circuit, and a second operational frequency range is determined 706 for the ECG circuit. A first decoupling element (or circuitry, etc.) can be selected 708 to be placed between the shared electrode and the antenna matching circuit, in order to filter out the second operational frequency range. A second decoupling element (or circuitry, etc.) can be selected 710 to be placed between the shared electrode and the ECG circuit, in order to filter out the first operational frequency range. Taking advantage of these different frequency ranges enables a decoupling circuit, or set of decoupling elements, to be used to pick out the frequency ranges of interest for each circuit, such as where there may be different or other circuits sharing the electrode as well. Once decoupling is in place, the antenna matching circuit and the ECG circuitry can be operated 712 concurrently. The antenna matching circuit can then be enabled 714 to transmit a signal and/or receive a signal using the shared electrode in the first operational frequency range, and the ECG circuit can be enabled to receive input from the shared electrode in the second operational frequency range, with minimal cross-talk between the frequency ranges across the decoupling circuitry. As mentioned, there may be different numbers of electrodes or circuitry that can be shared in various combinations within the scope of the various embodiments.

As mentioned, the various embodiments can be implemented as a system that includes one or more tracking devices for a given user. In some instances aspects of the embodiments may be provided as a service, which users can utilize for their devices. Other tracker providers may also subscribe or utilize such a service for their customers. In some embodiments an application programming interface (API) or other such interface may be exposed that enables collected body data, and other information, to be delivered to the service, which can process the information and send the results back down to the tracker, or related computing device, for access by the user. In some embodiments at least some of the processing may be done on the tracking or computing device itself, but processing by a remote system or service may allow for more robust processing, particularly for tracking devices with limited capacity or processing capability.

Figure 8A:
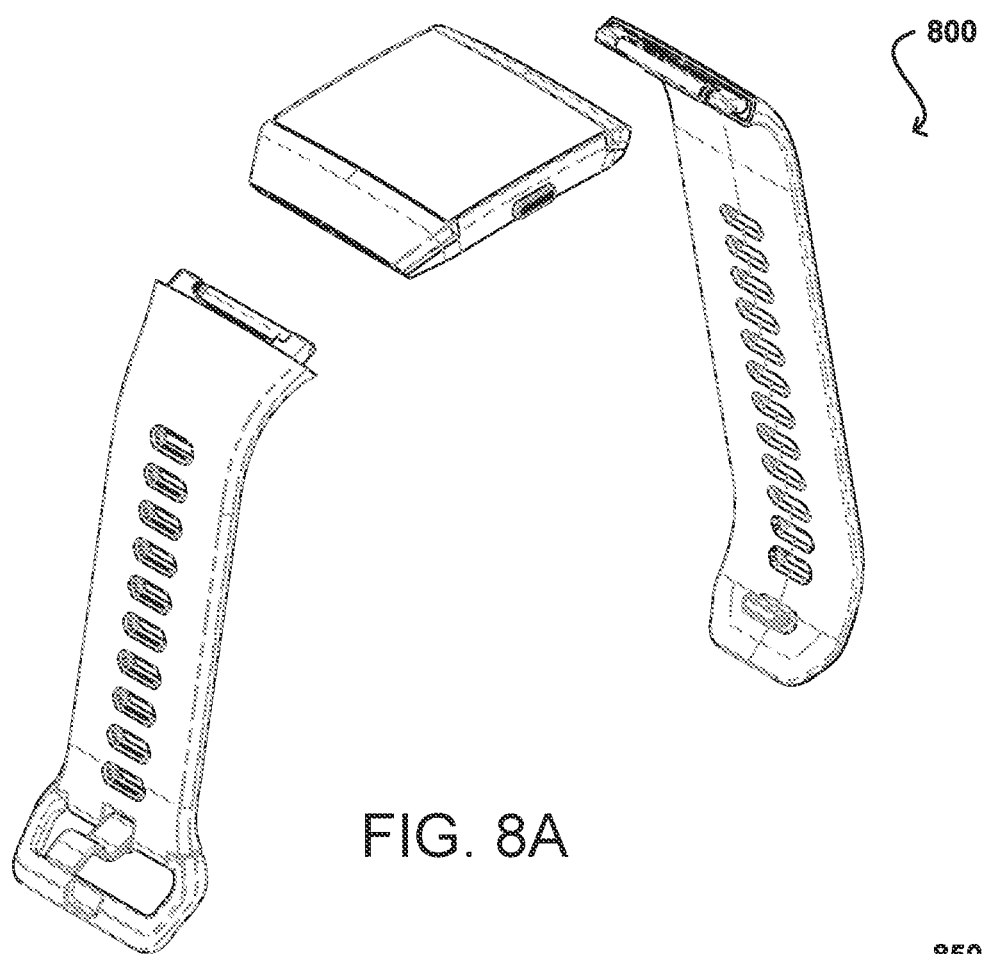
FIGS. 8A and 8B illustrate another example antenna design for a computing device that can be utilized in accordance with various embodiments.
Figure 8B:
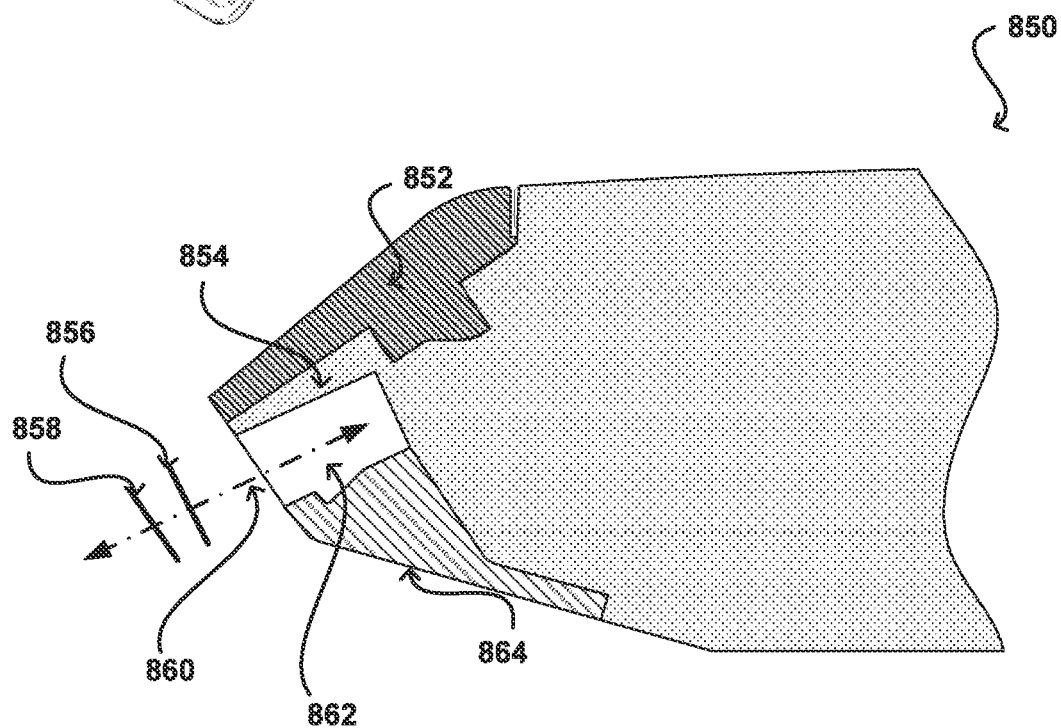

In some example embodiments, the housing of a device 800, such as a fitness tracker illustrated in FIG. 8A, may include a metallic body that forms at least a part of the boundaries of the cavity 862 and a metallic antenna in close proximity to the cavity 862. As illustrated in the view 850 of FIG. 8B, the antenna 852 is located above the metallic body 864. While many internal aspects of the fitness tracker have been omitted from this view, a non-metallic material 854, such as plastic, is illustrated as separating the antenna 852 from the metallic body 864. In some instances the performance of the antenna may decrease when metallic bodies are positioned within a particular threshold distance or zone from the antenna 852. This may be considered a "keep-out" zone which varies for different antennas. The metallic body 864 is positioned and shaped so that it is outside the keep-out zone of the antenna 852. Although the metallic body 864 is described as metallic, in some embodiments this aspect of the housing may not be metallic, but rather a polymer, a plastic, a composite, or other material that can form a portion of the housing with suitable strength and rigidity, for example. It was further discovered that when a metallic body was inserted into the cavity 862 and made contact with the metallic surface of the cavity 862, the inserted metallic body became an electric ground for the metallic body 864 which caused the inserted metallic body to be within the keep-out zone of the antenna 852 and adversely affected the performance of the antenna 852. However, it was discovered that if a metallic body was inserted into the cavity 862, was within the keep-out zone, but did not make contact with the metallic surfaces of the cavity 862, then the inserted metallic body did not adversely affect the performance of the antenna 852. Accordingly, some embodiments of the band latch mechanism disclosed herein are intended to be inserted into the cavity to enable a wristband to be connected to the housing without having a metallic body contact the metallic surfaces of the cavity while still maintaining an adequate connection to the housing and having sufficient robustness, resilience, and strength. Additional detail regarding such an implementation can be found in co-pending U.S. patent application Ser. No. 15/820,928, filed Nov. 22, 2017, and entitled "Band Latch Mechanism and Housing with Integrated Antenna," which is hereby incorporated herein in its entirety and for all purposes.

Figure 9:
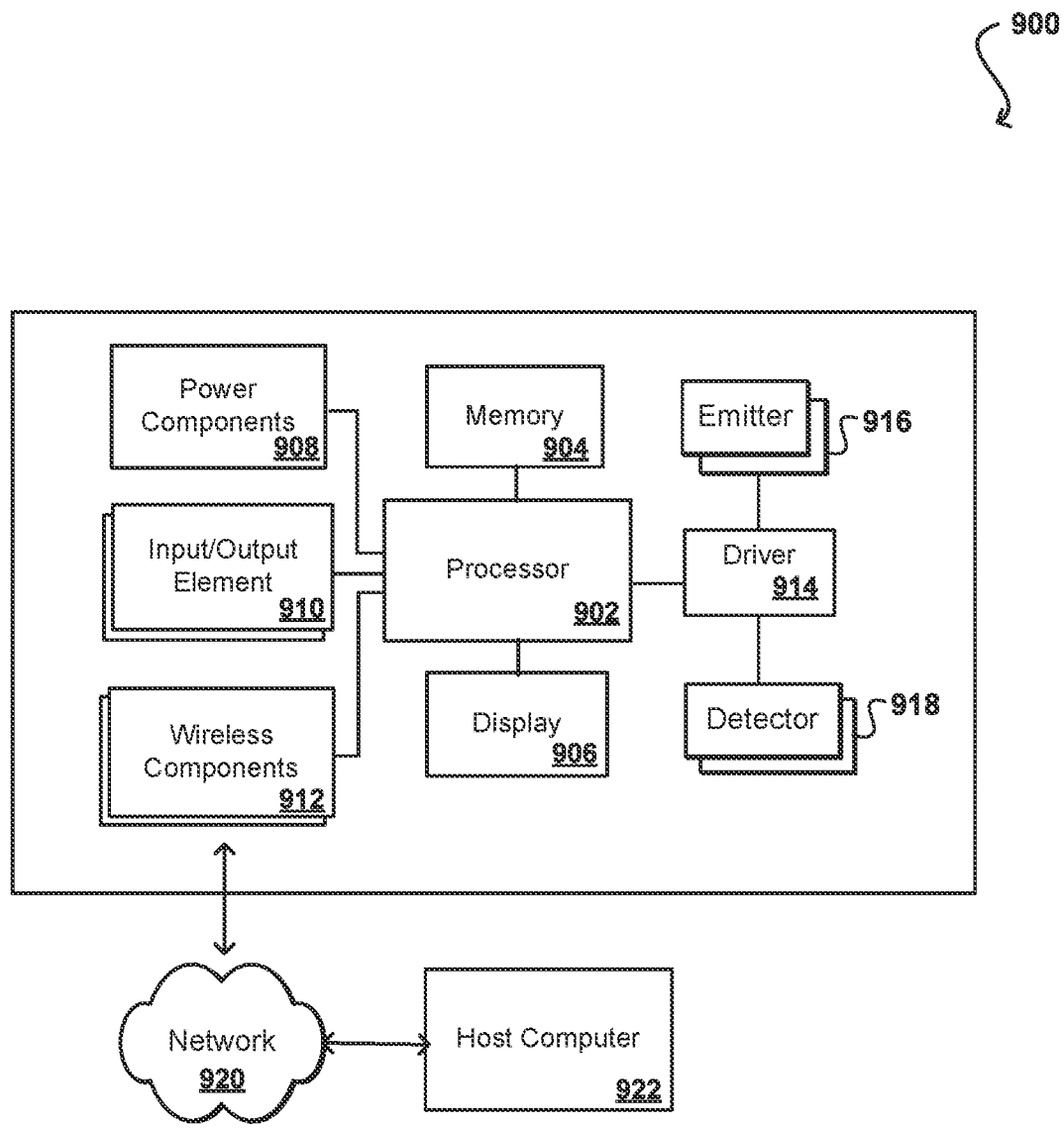
FIG. 9 illustrates components of an example computing device that can be utilized in accordance with various embodiments.

FIG. 9 illustrates components of an example cycle prediction system 900 that can be utilized in accordance with various embodiments. In this example, the device includes at least one processor 902, such as a central processing unit (CPU) or graphics processing unit (GPU) for executing instructions that can be stored in a memory device 904, such as may include flash memory or DRAM, among other such options. As would be apparent to one of ordinary skill in the art, the device can include many types of memory, data storage, or computer-readable media, such as data storage for program instructions for execution by a processor. The same or separate storage can be used for images or data, a removable memory can be available for sharing information with other devices, and any number of communication approaches can be available for sharing with other devices. The device typically will include some type of display 906, such as a touch screen, organic light emitting diode (OLED) display, or liquid crystal display (LCD), although devices might convey information via other means, such as through audio speakers or projectors.

A tracker or similar device will include at least one motion detection sensor, which as illustrated can include at least one I/O element 910 of the device. Such a sensor can determine and/or detect orientation and/or movement of the device. Such an element can include, for example, an accelerometer, inertial sensor, altimeter, or gyroscope operable to detect movement (e.g., rotational movement, angular displacement, tilt, position, orientation, motion along a non-linear path, etc.) of the device. An orientation determining element can also include an electronic or digital compass, which can indicate a direction (e.g., north or south) in which the device is determined to be pointing (e.g., with respect to a primary axis or other such aspect). A device may also include an I/O element 910 for determining a location of the device (or the user of the device). Such a positioning element can include or comprise a GPS or similar location-determining element (s) operable to determine relative coordinates for a position of the device. Positioning elements may include wireless access points, base stations, etc., that may either broadcast location information or enable triangulation of signals to determine the location of the device. Other positioning elements may include QR codes, barcodes, RFID tags, NFC tags, etc., that enable the device to detect and receive location information or identifiers that enable the device to obtain the location information (e.g., by mapping the identifiers to a corresponding location). Various embodiments can include one or more such elements in any appropriate combination. The I/O elements may also include one or more biometric sensors, optical sensors, barometric sensors (e.g., altimeter, etc.), and the like.

As mentioned above, some embodiments use the element (s) to track the location and/or motion of a user. Upon determining an initial position of a device (e.g., using GPS), the device of some embodiments may keep track of the location of the device by using the element(s), or in some instances, by using the orientation determining element(s) as mentioned above, or a combination thereof. As should be understood, the algorithms or mechanisms used for determining a position and/or orientation can depend at least in part upon the selection of elements available to the device. The example device also includes one or more wireless components 912 operable to communicate with one or more electronic devices within a communication range of the particular wireless channel. The wireless channel can be any appropriate channel used to enable devices to communicate wirelessly, such as Bluetooth, cellular, NFC, or Wi-Fi channels. It should be understood that the device can have one or more conventional wired communications connections as known in the art. The device also includes one or more power components 908, such as may include a battery operable to be recharged through conventional plug-in approaches, or through other approaches such as inductive or wireless charging through proximity with a power mat or other such device. In some embodiments the device can include at least one additional input/output device 910 able to receive conventional input from a user. This conventional input can include, for example, a push button, touch pad, touch screen, wheel, joystick, keyboard, mouse, keypad, or any other such device or element whereby a user can input a command to the device. These I/O devices could even be connected by a wireless infrared or Bluetooth or other link as well in some embodiments. Some devices also can include a microphone or other audio capture element that accepts voice or other audio commands. For example, a device might not include any buttons at all, but might be controlled only through a combination of visual and audio commands, such that a user can control the device without having to be in contact with the device.

As mentioned, many embodiments will include at least some combination of one or more emitters 916 and one or more detectors 918 for measuring data for one or more metrics of a human body, such as for a person wearing the tracker device. In some embodiments this may involve at least one imaging element, such as one or more cameras that are able to capture images of the surrounding environment and that are able to image a user, people, or objects in the vicinity of the device. The image capture element can include any appropriate technology, such as a CCD image capture element having a sufficient resolution, focal range, and viewable area to capture an image of the user when the user is operating the device. Methods for capturing images using a camera element with a computing device are well known in the art and will not be discussed herein in detail. It should be understood that image capture can be performed using a single image, multiple images, periodic imaging, continuous image capturing, image streaming, etc. Further, a device can include the ability to start and/or stop image capture, such as when receiving a command from a user, application, or other device. The example device includes emitters 916 and detectors 918 capable of being used for obtaining other biometric data, which can be used with example circuitry discussed herein.

If included, a display 906 may provide an interface for displaying data, such as heart rate (HR), ECG data, blood oxygen saturation ($SpO_2$) levels, and other metrics of the user. In an embodiment, the device includes a wristband and the display is configured such that the display faces away from the outside of a user's wrist when the user wears the device. In other embodiments, the display may be omitted and data detected by the device may be transmitted using the wireless networking interface via near-field communication (NFC), Bluetooth, Wi-Fi, or other suitable wireless communication protocols over at least one network 920 to a host computer 922 for analysis, display, reporting, or other such use.

The memory 904 may comprise RAM, ROM, FLASH memory, or other non-transitory digital data storage, and may include a control program comprising sequences of instructions which, when loaded from the memory and executed using the processor 902, cause the processor 902 to perform the functions that are described herein. The emitters 916 and detectors 918 may be coupled to a bus directly or indirectly using driver circuitry by which the processor 902 may drive the light emitters 916 and obtain signals from the light detectors 918. The host computer 922 communicates with the wireless networking components 912 via one or more networks 920, which may include one or more local area networks, wide area networks, and/or internet, using any of terrestrial or satellite links. In some embodiments, the host computer 922 executes control programs and/or application programs that are configured to perform some of the functions described herein.

In various embodiments, approaches discussed herein may be performed by one or more of: firmware operating on a monitoring or tracker device or a secondary device, such as a mobile device paired to the monitoring device, a server, host computer, and the like. For example, the monitoring device may execute operations relating to generating signals that are uploaded or otherwise communicated to a server that performs operations for removing the motion components and creating a final estimate value for physiological metrics. Alternatively, the monitoring device may execute operations relating to generating the monitoring signals and measuring the motion components to produce a final estimate value for physiological metrics local to the monitoring device. In this case, the final estimate may be uploaded or otherwise communicated to a server such as host computer that performs other operations using the estimate.

An example monitoring or tracker device can collect one or more types of physiological and/or environmental data from one or more sensor(s) and/or external devices and communicate or relay such information to other devices (e.g., host computer or another server), thus permitting the collected data to be viewed, for example, using a web browser or network-based application. For example, while being worn by the user, a tracker device may perform biometric monitoring via calculating and storing the user's step count using one or more sensor(s). The tracker device may transmit data representative of the user's step count to an account on a web service (e.g., www.fitbit.com), computer, mobile phone, and/or health station where the data may be stored, processed, and/or visualized by the user. The tracker device may measure or calculate other physiological metric(s) in addition to, or in place of, the user's step count. Such physiological metric(s) may include, but are not limited to: energy expenditure, e.g., calorie burn; floors climbed and/or descended; HR; heartbeat waveform; HR variability; HR recovery; respiration, $SpO_2$, blood volume, blood glucose, skin moisture and skin pigmentation level, location and/or heading (e.g., via a GPS, global navigation satellite system (GLONASS), or a similar system); elevation; ambulatory speed and/or distance traveled; swimming lap count; swimming stroke type and count detected; bicycle distance and/or speed; blood glucose; skin conduction; skin and/or body temperature; muscle state measured via electromyography; brain activity as measured by electroencephalography; weight; body fat; caloric intake; nutritional intake from food; medication intake; sleep periods (e.g., clock time, sleep phases, sleep quality and/or duration); pH levels; hydration levels; respiration rate; and/or other physiological metrics.

An example tracker or monitoring device may also measure or calculate metrics related to the environment around the user (e.g., with one or more environmental sensor(s)), such as, for example, barometric pressure, weather conditions (e.g., temperature, humidity, pollen count, air quality, rain/snow conditions, wind speed), light exposure (e.g., ambient light, ultra-violet (UV) light exposure, time and/or duration spent in darkness), noise exposure, radiation exposure, and/or magnetic field exposure. Furthermore, a tracker device (and/or the host computer and/or another server) may collect data from one or more sensors of the device, and may calculate metrics derived from such data. For example, a tracker device may calculate the user's stress or relaxation levels based on a combination of HR variability, skin conduction, noise pollution, and/or sleep quality. In another example, a tracker device may determine the efficacy of a medical intervention, for example, medication, based on a combination of data relating to medication intake, sleep, and/or activity. In yet another example, a tracker device may determine the efficacy of an allergy medication based on a combination of data relating to pollen levels, medication intake, sleep and/or activity. These examples are provided for illustration only and are not intended to be limiting or exhaustive.

An example monitoring device may include a computer-readable storage media reader, a communications device (e.g., a modem, a network card (wireless or wired), an infrared communication device) and working memory as described above. The computer-readable storage media reader can be connected with, or configured to receive, a computer-readable storage medium representing remote, local, fixed and/or removable storage devices as well as storage media for temporarily and/or more permanently containing, storing, transmitting and retrieving computer-readable information. A monitoring system and various devices also typically will include a number of software applications, modules, services or other elements located within at least one working memory device, including an operating system and application programs such as a client application or Web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Storage media and other non-transitory computer readable media for containing code, or portions of code, can include any appropriate media known or used in the art, such as but not limited to volatile and non-volatile, removable and non-removable media implemented in any method or technology for storage of information such as computer readable instructions, data structures, program modules or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices or any other medium which can be used to store the desired information and which can be accessed by a system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

What is claimed is:

1. A wearable device comprising:
    a biometric circuit configured to monitor one or more biometrics of a user wearing the wearable device;
    a first conductive element;
    a first decoupling element configured to selectively couple the first conductive element to the biometric circuit such that the first conductive element operates as an electrode for the biometric circuit;
    a second decoupling element configured to selectively couple the first conductive element to an electrical ground such that the first conductive element operates as an antenna; and
    a first antenna matching circuit coupled between the second decoupling element and the electrical ground.

2. The wearable device of claim 1, wherein the first decoupling element comprises a resistor, a capacitor, or an inductor.

3. The wearable device of claim 1, wherein the second decoupling element comprises a capacitor.

4. The wearable device of claim 1, wherein the biometric circuit comprises an electrocardiogram (ECG) circuit.

5. The wearable device of claim 1, further comprising:
    a second antenna matching circuit that is separate from the first antenna matching circuit; and
    a second conductive element that is different from the first conductive element, the second conductive element electrically coupled to the second antenna matching circuit.

6. The wearable device of claim 1, wherein the first conductive element is part of a housing of the wearable device.

7. The wearable device of claim 1, wherein the antenna comprises a parasitic antenna.

8. An electronic device comprising:
    a biometric circuit configured to monitor one or more biometrics of a user;
    a first conductive element;
    a first decoupling element configured to selectively couple the first conductive element to the biometric circuit such that the first conductive element operates as an electrode for the biometric circuit;
    a second decoupling element configured to selectively couple the first conductive element to an electrical ground such that the first conductive element operates as an antenna; and
    a first antenna matching circuit coupled between the second decoupling element and the electrical ground.

9. The electronic device of claim 8, wherein the first decoupling element comprises a resistor, a capacitor, or an inductor.

10. The electronic device of claim 8, wherein the second decoupling element comprises a capacitor.

11. The electronic device of claim 8, wherein the biometric circuit comprises an electrocardiogram (ECG) circuit.

12. The electronic device of claim 8, further comprising:
    a second antenna matching circuit that is separate from the first antenna matching circuit; and
    a second conductive element that is different from the first conductive element, the second conductive element electrically coupled to the second antenna matching circuit.

13. The electronic device of claim 8, wherein the first conductive element is part of a housing of the electronic device.

14. The electronic device of claim 8, wherein the antenna comprises a parasitic antenna.

* * * * *